United States Patent [19]

Leichnitz

[11] Patent Number: 4,460,544
[45] Date of Patent: Jul. 17, 1984

[54] TEST TUBE FOR THE MEASUREMENT OF OIL MISTS

[75] Inventor: Kurt Leichnitz, Gross Grönau, Fed. Rep. of Germany

[73] Assignee: Drägerwerk AG, Fed. Rep. of Germany

[21] Appl. No.: 486,086

[22] Filed: Apr. 18, 1983

[30] Foreign Application Priority Data

Jun. 25, 1982 [DE] Fed. Rep. of Germany ....... 3123742

[51] Int. Cl.³ .................... G01N 21/78; G01N 33/28
[52] U.S. Cl. ...................................... 422/59; 422/60; 422/86; 436/139
[58] Field of Search .................. 422/59, 60, 83, 86, 422/88; 436/139

[56] References Cited

U.S. PATENT DOCUMENTS 4,272,479 6/1981 Huneke et al. ............... 422/60 X
4,300,910 11/1981 Pannwitz ...................... 422/59 X

OTHER PUBLICATIONS

Leichnitz et al., Ann. Occup. Hyg., vol. 24, No. 1, pp. 43–53, 1981.

Primary Examiner—Arnold Turk
Attorney, Agent, or Firm—McGlew and Tuttle

[57] ABSTRACT

A device for the measurement of oil mists in a test gas comprises a glass tube which has ends which are openable such as by breaking off to permit a test gas to be directed therethrough. The glass tube contains in order in the direction of flow: a breakable ampoule filled with sulfuric acid, a particulate air filter, a distributor layer of quartz glass grit, and an indicator layer of deactivated silica gel. To effect a testing of a test gas it is directed through the glass tube after the tube ends have been broken off. Any oil mist and gas will be engaged with the filter layer. Thereafter, the ampoule is broken and sulfuric acid flows to the filter where it reacts with the mist and causes a defined color reading. In comparison with a color standard shows the oil concentration of the test gas.

3 Claims, 1 Drawing Figure

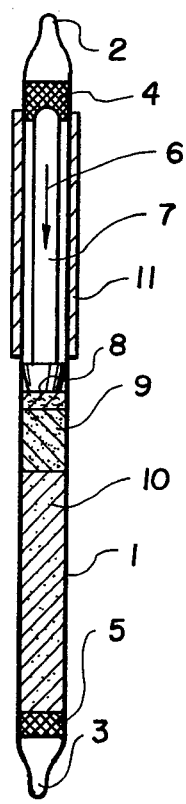

TEST TUBE FOR THE MEASUREMENT OF OIL MISTS

FIELD AND BACKGROUND OF THE INVENTION

This invention relates in general to devices for testing gases and in particular to a new and useful test tube for the selective measurement of oil mists in a test gas.

According to the list of admissible limit value of air pollution, for working places (Threshold Limit Values, USA, 1980) the corresponding value for oil mists is 5 mg/cu m. It is explicitly pointed out that the sampling has to be effected according to a method that does not collect the oil vapor.

The admissible limit values for oil mists and oil vapor differ by several orders of magnitude. In order to permit a reliable evaluation of the health hazards in working places, it is thus absolutely necessary to determine the oil mist content of the air. But since oil mist and oil vapor exist primarily side by side, it is necessary to use an analytical method which ensures the selective determination of the oil mist in the presence of oil vapors.

A known test tube measures the oil content, that is, the sum of oil vapor and oil mist in gases. It contains in a fused glass tube in the direction of flow an ampoule with concentrated sulfuric acid and an adsorption layer of activated silica gel with a catalyst. At the level of the ampoule the glass tube is sheathed on the outside by a shrink-on tubing. In use, the test gas is passed through after opening the tube ends. Subsequently, the ampoule is broken by bending the glass tube and its contents is distributed over the adsorption layer.

The oil adsorbed there is converted to dark-colored reaction products whose color intensity is evaluated. The amount of oil found is composed of the partial amounts introduced into the test tube in the form of oil vapor and oil mist. (Directions of Use 6728371, December 1979, Draegerwerk AG, Lubeck)

Since the oil vapors are likewise retained in the activated silica gel, it is not possible to determine from the reading the portion of hazardous oil mists.

A known test tube for measuring chromate-and chromic acid aerosols in air contains, in the direction of flow, in a glass tube with a break-off tips: a breakable ampoule, a filter paper terminating the tube wall, as well as (1) a granular reagent layer of inert quartz and (2) a reagent layer of sorption-active silica gel, which is followed by a collecting layer, again of inert quartz. At the level of the ampoule the glass tube is sheathed with a shrink-on tubing. The ampoule contains diluted sulfuric acid. After passing through the test air and depositing the aerosols contained therein on the filter paper, the ampoule is broken by bending the glass tube and the acid is thrown in the direction of the filling layers. The aerosols deposited on the filter paper are dissolved and introduced into the second reagent layer together with the reagent, likewise dissolved from the first reagent layer. Here a color reaction to a violet color takes place, whose intensity is evaluated (German Pat. No. 2,913,283).

This test tube would not be suitable for measuring oil mists, apart from the unsuitable reagents because the oil vapors existing at the same time in the sorption-active silica gel of the second reagent layer are retained and would be indicated together with the reaction oil mists.

SUMMARY OF THE INVENTION

The invention provides a simple, selective measuring method for oil mists in test gas which can be carried out without further preparations even by less qualified workers.

The solution utilizes the test tube method whose principle meets the requirements for its easy use in an advantageous manner.

Accordingly, it is an object of the invention to provide a device for the measurement of oil mists in a test gas which comprises a glass tube which has ends which are openable such as by breaking off to permit a test gas to be directed therethrough. The glass tube contains in order proceeding in the direction of the flow: a breakable ampoule filled with sulfuric acid, a particulate air filter, a distributor layer of quartz glass grit, and an indicator layer of deactivated silica gel.

The test tube method is generally used and permits in a simple manner, e.g. to carry out a test of the ambient air for monitoring the working place. The measuring result is immediately available at the site of the measurement without delay.

For the measurement it is merely necessary to open the test tube tips in a first operation and then to pump the test gas with the known suction pump through the test tube and through the particulate air filter. The particulate air filter retains only the oil mists, any oil vapor contained in the test gas leaves the test tube without any reaction, after passing through the other layers, together with the test gas.

Accordingly, it is an object of the invention to provide a device for the measurement of oil mist which includes a glass tube which has severable ends, an interior ampoule which may be broken to cause sulfuric acid to have a color indication after a test gas is first directed through the tube.

A further object of the invention is to provide a device for the measurement of oil mists which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

The only FIGURE of the drawing is a sectional view of a glass tube for testing gases and constructed in accordance with the invention.

DESCRIPTION OF THE PREFERRED EMBODIMENT

Referring to the drawing in particular, the invention embodied therein comprises a device for measuring oil mists in a test gas which comprises a glass tube 1 having ends which are openable such as by being broken off at tips 2 and 3 to permit a test gas to be directed therethrough. The glass tube contains, in order in respect to the direction of test gas flow therethrough, a breakable ampoule filled with sulfuric acid 7, a particulate air filter 8, a distributor layer of quartz glass grit 9 and an indicator layer of deactivated silica gel 10.

The device includes a glass tube 1 with the two break-off tips 2 and 3. The filling glass tube 1 is held vibration-proof between holders 4 and 5 in the sectors provided for this purpose. In the direction of flow 6 of the test gas, the tube 1 contains: the breakable ampoule 7 which is filled with sulfuric acid, the mist filter 8 of glass fibers, the granular distributor layer 9 of quartz glass grit, and of the granular indicator layer 10 of deactivated silica gel. Glass tube 1 is sheathed with shrink-on tubing 11 covering the range of ampoule 7.

The measurement is effected in two operations:

1. After tips 2 and 3 have been broken off, the test tube is introduced into the known suction pump, and then the gas to be tested is pumped with 100 strokes in the direction of flow 6 through the test tube. The oil mists contained in the test gas are deposited on mist filter 8. The simultaneously existing oil vapor flows without reaction both through mist filter 8 and through distributor layer 9 and indicator layer 10 and leaves the test tube again together with the test gas through the open tip 3.

2. With glass tube 1 is also broken at this point ampoule 7 in its longitudinal direction. The sulfuric acid is then thrown in the direction of mist filter 8. The sulfuric acid dissolves the oil, turning it brown, and flushes the solution through distributor layer 9, where it is evenly distributed into indicator layer 10. It remains there and causes a defined color reading. The intensity of the discoloration is proportional to the amount of oil mist filtered out from the test gas. A comparison with the enclosed color standard shows the oil concentration to be determined in the test gas.

While a specific embodiment of the invention has been shown and described in detail to illustrate the application of the principles of the invention, it will be understood that the invention may be embodied otherwise without departing from such principles.

What is claimed is:

1. A device for the measurement of oil mists in a test gas, comprising a glass tube having ends which are openable to permit a test gas to be directed therethrough, said glass tube being filled in order with respect to the direction of intended gas flow therethrough with: a breakable ampoule filled with sulfuric acid, a particulate air filter, a distributor layer of quartz glass grit, and an indicator layer of deactivated silica gel.

2. A device according to claim 1, wherein said particulate filter is a filter paper of glass fibers bearing on said tube wall.

3. A device according to claim 2, including a tube shrunk fit over said glass tube in the vicinity of said ampoule.

* * * * *